(12) United States Patent
Nemer et al.

(10) Patent No.: US 9,518,968 B2
(45) Date of Patent: Dec. 13, 2016

(54) IN SITU HEATED OXYGEN PROBE WITH INTRINSICALLY SAFE OUTPUT

(71) Applicant: Rosemount Analytical Inc., Solon, OH (US)

(72) Inventors: Joseph C. Nemer, Mayfield Heights, OH (US); Mark D. Stojkov, Parma, OH (US)

(73) Assignee: Rosemount Analytical Inc., Solon, OH (US)

( * ) Notice: Subject to any disclaimer, the term of this patent is extended or adjusted under 35 U.S.C. 154(b) by 397 days.

(21) Appl. No.: 14/275,152

(22) Filed: May 12, 2014

(65) Prior Publication Data

US 2014/0338422 A1 Nov. 20, 2014

Related U.S. Application Data

(60) Provisional application No. 61/824,627, filed on May 17, 2013.

(51) Int. Cl.
*G01N 7/00* (2006.01)
*G01N 33/00* (2006.01)
*G01N 27/406* (2006.01)

(52) U.S. Cl.
CPC ...... *G01N 33/0009* (2013.01); *G01N 27/4067* (2013.01)

(58) Field of Classification Search
CPC ..... G01M 99/008; G01M 13/00; G01M 99/00
USPC ...................................... 73/865.9
See application file for complete search history.

(56) References Cited

U.S. PATENT DOCUMENTS

| | | | |
|---|---|---|---|
| 5,053,200 A | * | 10/1991 | Schaeffer ............. G01N 1/2258 138/42 |
| 5,136,630 A | | 8/1992 | Breneman et al. |
| 6,487,912 B1 | | 12/2002 | Behm et al. |
| 2004/0089075 A1 | | 5/2004 | Behm et al. |
| 2004/0113635 A1 | | 6/2004 | Masuda et al. |
| 2011/0012040 A1 | | 1/2011 | Bailey |

OTHER PUBLICATIONS

First Examination Report for Australian Patent Application No. 2014265625 dated Mar. 31, 2016, 2 pages.

(Continued)

*Primary Examiner* — Hezron E Williams
*Assistant Examiner* — Rodney T Frank
(74) *Attorney, Agent, or Firm* — Christopher R. Christenson; Kelly, Holt & Christenson PLLC

(57) ABSTRACT

An in situ oxygen analyzer having an intrinsically-safe output and a heated probe is provided. The probe is extendable into a source of process gas and has an oxygen sensor and heater disposed therein. The heater is configured to heat the oxygen sensor to a temperature sufficient to operate the oxygen sensor. A housing is coupled to the probe and has first and second chambers. The first chamber is explosion-rated and includes non-intrinsically safe circuitry coupled to the heater to energize the heater. The second chamber contains only intrinsically-safe circuitry that complies with an intrinsically-safe specification. The first and second chambers are isolated from one another. The non-intrinsically-safe circuitry is coupled to the intrinsically-safe circuitry through an energy-limiting isolator.

14 Claims, 3 Drawing Sheets

(56) References Cited

OTHER PUBLICATIONS

"Two-Wire In Situ Oxygen Analyzer (550° to 1400° C.)", Product Data Sheet, PDS 106-581.A01, Sep. 2007, Model 5081FG, Rosemount Analytical, Emerson Process Management, 6 pages.
International Search Report and Written Opinion from International Application No. PCT/US2014/037822, mailing date: Sep. 17, 2014. 11 pages.

* cited by examiner

IN SITU HEATED OXYGEN PROBE WITH INTRINSICALLY SAFE OUTPUT

CROSS-REFERENCE TO RELATED APPLICATION

The present application is based on and claims the benefit of U.S. Provisional Patent Application Ser. No. 61/824,627, filed May 17, 2013, the content of which is hereby incorporated in its entirety.

BACKGROUND

Industrial process industries often rely on energy sources that include one or more combustion processes. Such combustion processes include operation of a furnace or boiler to generate energy from combustion, which is then used for the process. While combustion provides relatively low-cost energy, its use is typically regulated and combustion efficiency is sought to be maximized. Accordingly, one goal of the process management industry is to reduce the production of greenhouse gases by maintaining maximum combustion efficiency of existing furnaces and boilers.

In situ flue gas analyzers are commonly used for monitoring, optimizing and/or controlling combustion processes. Typically, these analyzers employ a zirconium oxide sensor to measure excess oxygen in the flue gas. Such an oxygen sensor is known and uses a principle of operation based on the Nernst equation. This principle of operation requires that the sensor cell be maintained at an elevated operating temperature. Typically, such elevated temperatures are achieved using a heater that is powered by an analyzer's electronics. In situ flue gas analyzers are particularly advantageous because they have no moving parts or sampling apparatus resulting in an extremely reliable probe that requires very little maintenance.

Some operators of combustion processes have applications that involve hazardous gases in the process itself or in the ambient gases in the area where the analyzer's electronics are installed. These operators are concerned that the cell heater may serve as a source of ignition to these hazardous gases inside the process or that the electronics can provide ignition to hazardous process or ambient gases that may be present. As a result of these concerns, these users must purchase analyzers with costly protection features.

When hazardous gases are present, there are typically two ways in which protection can be provided: explosion-proof enclosures and/or intrinsically safe circuitry.

When electronics are housed within explosion-proof enclosures, such enclosures can prevent the gases from entering the internal chamber of the enclosure. Additionally, if such gases do enter the enclosure and cause an explosion, the flame will not be able to propagate outside of the enclosure. One example of an explosion proof rating is an ATEX certification to EEx d IIB T6 standards EN50015 and EN50018 for potentially explosive atmospheres Parts 1 and 5.

The other protection scheme is to make the electronics intrinsically safe. When the electronics are intrinsically safe, they inherently cannot generate the required temperature or spark to generate an explosion, even under fault conditions. An example of an intrinsic safety specification is the standard promulgated by Factory Mutual Research in October 1998 entitled APPROVAL STANDARD INTRINSICALLY SAFE APPARATUS AND ASSOCIATED APPARATUS FOR USE IN CLASS I, II, AND III, DIVISION 1 HAZARDOUS (CLASSIFIED) LOCATIONS, CLASS NUMBER 3610. Intrinsic safety requirements generally specify such low energy levels that compliance is simply not possible with circuitry that involves high voltages, high currents, and/or high wattage, such as AC circuits.

One particular device that has been used in the past for explosive environments is sold under the trade designation Model 5081FG Two-Wire In Situ Oxygen Analyzer, available from Emerson Process Management. This device utilizes a zirconium oxide sensor to measure excess oxygen in combustion processes. However, the analyzer eliminates the use of a cell heater and instead uses high process temperatures to heat the zirconium oxide sensor cell to the temperature required by the Nernst equation for operation. The analyzer's electronics are intrinsically safe, and can be powered by 4-20 mA signal wires. While the Model 5081 FG has proved useful for measuring oxygen in or proximate hazardous locations. its use has been limited to applications that generate enough process heat to maintain the zirconium oxide sensor at the requisite elevate temperature. Additionally, when process heat is required for sensor operation, useful sensor data is not available until the process has sufficiently heated the sensor. Thus, the ability to measure oxygen during system startup has been limited for in situ oxygen probes that have intrinsically safe output.

Providing an in situ oxygen probe with an intrinsically safe output that could function at lower temperatures and/or during system startup would increase the applications to which such devices could be applied.

SUMMARY

An in situ oxygen analyzer having an intrinsically-safe output and a heated probe is provided. The probe is extendable into a source of process gas and has an oxygen sensor and heater disposed therein. The heater is configured to heat the oxygen sensor to a temperature sufficient to operate the oxygen sensor. A housing is coupled to the probe and has first and second chambers. The first chamber is explosion-rated and includes non-intrinsically safe circuitry coupled to the heater to energize the heater. The second chamber contains only intrinsically-safe circuitry that complies with an intrinsically-safe specification. The first and second chambers are isolated from one another. The non-intrinsically-safe circuitry is coupled to the intrinsically-safe circuitry through an energy-limiting isolator.

DETAILED DESCRIPTION OF ILLUSTRATIVE EMBODIMENTS

Figure 1:
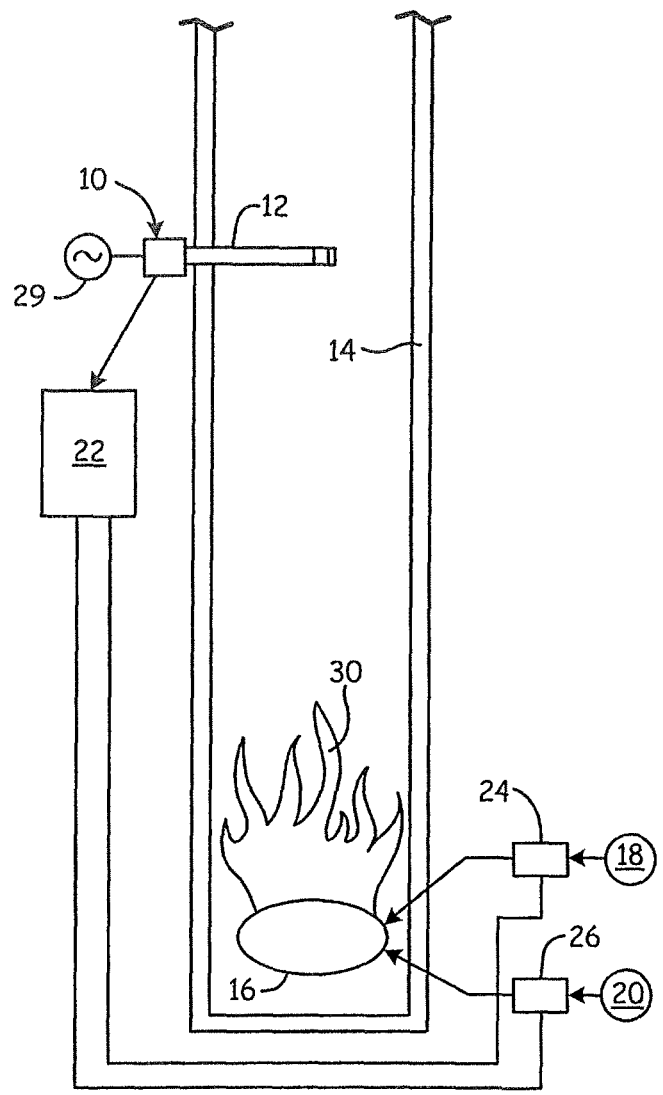
FIG. 1 is a diagrammatic view of an in situ oxygen probe with which embodiments of the present invention are particularly useful.

FIG. 1 is a diagrammatic view of an in situ flue oxygen probe operating in a combustion process. One example of such a device 10 is that sold under the trade designation Model 6888 In Situ Flue Gas Oxygen Transmitter available from Emerson Process Management. Analyzer 10 includes a probe assembly 12 that is disposed within a stack or flue 14 and measures oxygen in the combustion gases.

Burner 16 is operably coupled to a source of air or oxygen 18 and a source 20 of combustible fuel. Each of sources 18 and 20 is preferably coupled to burner 16 through a respective valve 24, 26 to deliver a controlled amount of oxygen and/or fuel to burner 16 in order to control the combustion process. Analyzer 10 measures the amount of oxygen in the combustion exhaust flow and provides an indication of the oxygen level to combustion controller 22. Controller 22 controls one or both of valves 24, 26 to provide closed loop combustion control. Analyzer 10 includes an oxygen sensor that must operate at elevated temperatures in order to function properly. One example of such an oxygen sensor is a zirconium oxide-based oxygen sensor, which provides an electrical signal indicative of oxygen concentration, content or percentage in the exhaust.

Zirconium oxide sensors operate at a temperature of about 700° Celsius and thus analyzer 10 includes, within probe assembly 12, an electrical heater (shown in FIG. 3) that is operably coupled to AC power source 29. The oxygen sensor within probe 12 is similar in technology to oxygen sensors found in automobiles. Such sensors are highly effective in permitting control systems to maintain optimum fuel to ratios in order to achieve high efficiency, low $NO_x$ production, and also the least amount of greenhouse gas emissions possible.

Figure 2:
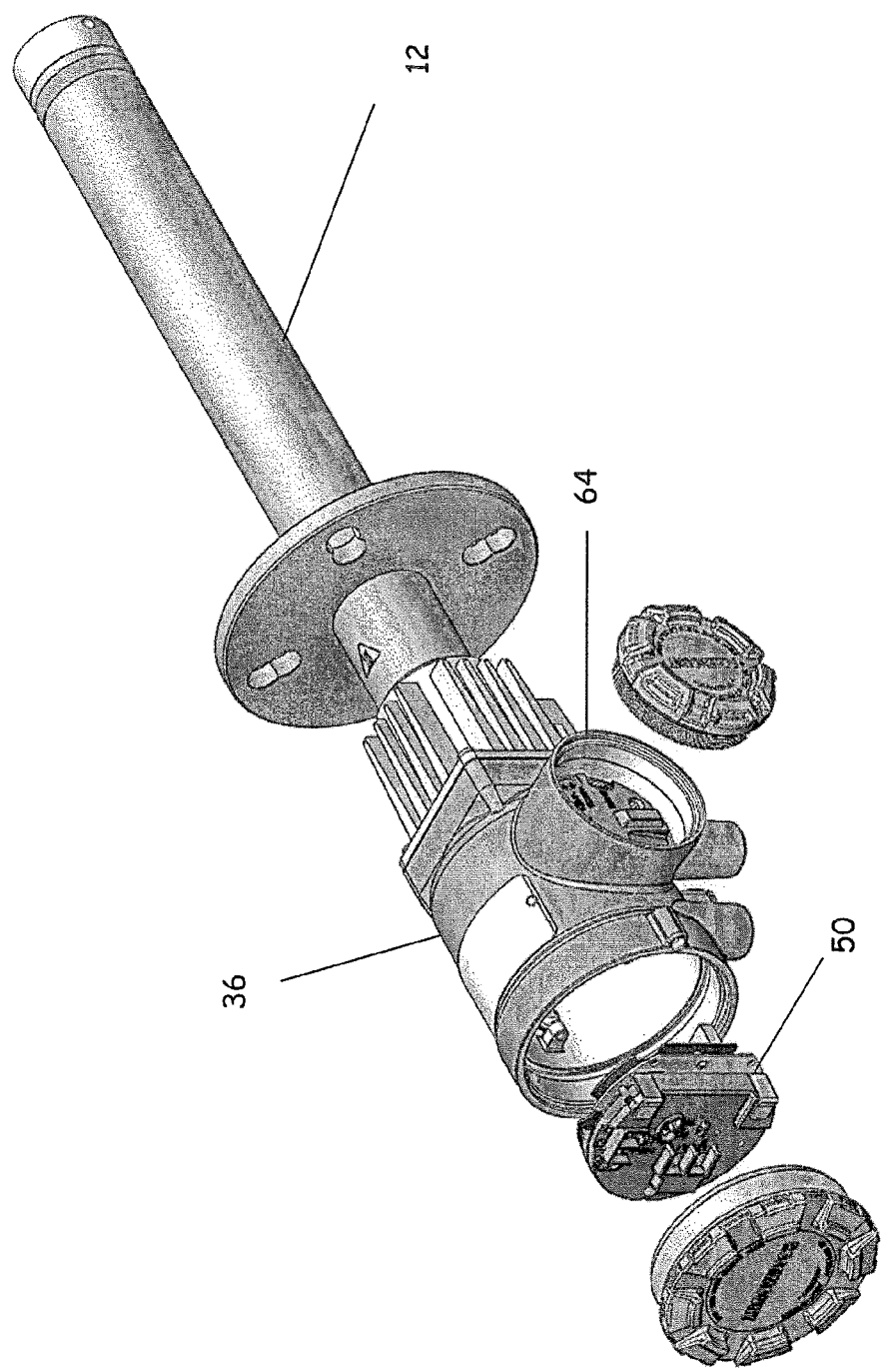
FIG. 2 is a diagrammatic perspective view of an in situ heated oxygen probe in accordance with an embodiment of the present invention.

FIG. 2 is a diagrammatic perspective view of an in situ flue heated oxygen probe in accordance with an embodiment of the present invention. Probe assembly 12 is generally configured to house a sensor core assembly which includes diffuser disposed proximate end 32. The measurement cell within probe 12 is operable at an elevated temperature. The measurement cell and heater within probe 12 are electrically coupled to analyzer electronics (shown in FIG. 3) within electronics housing 36. Analyzer electronics are configured to obtain a measurement from the measurement cell and provides suitable signal conditioning in order to provide a signal representing flue gas oxygen.

Figure 3:
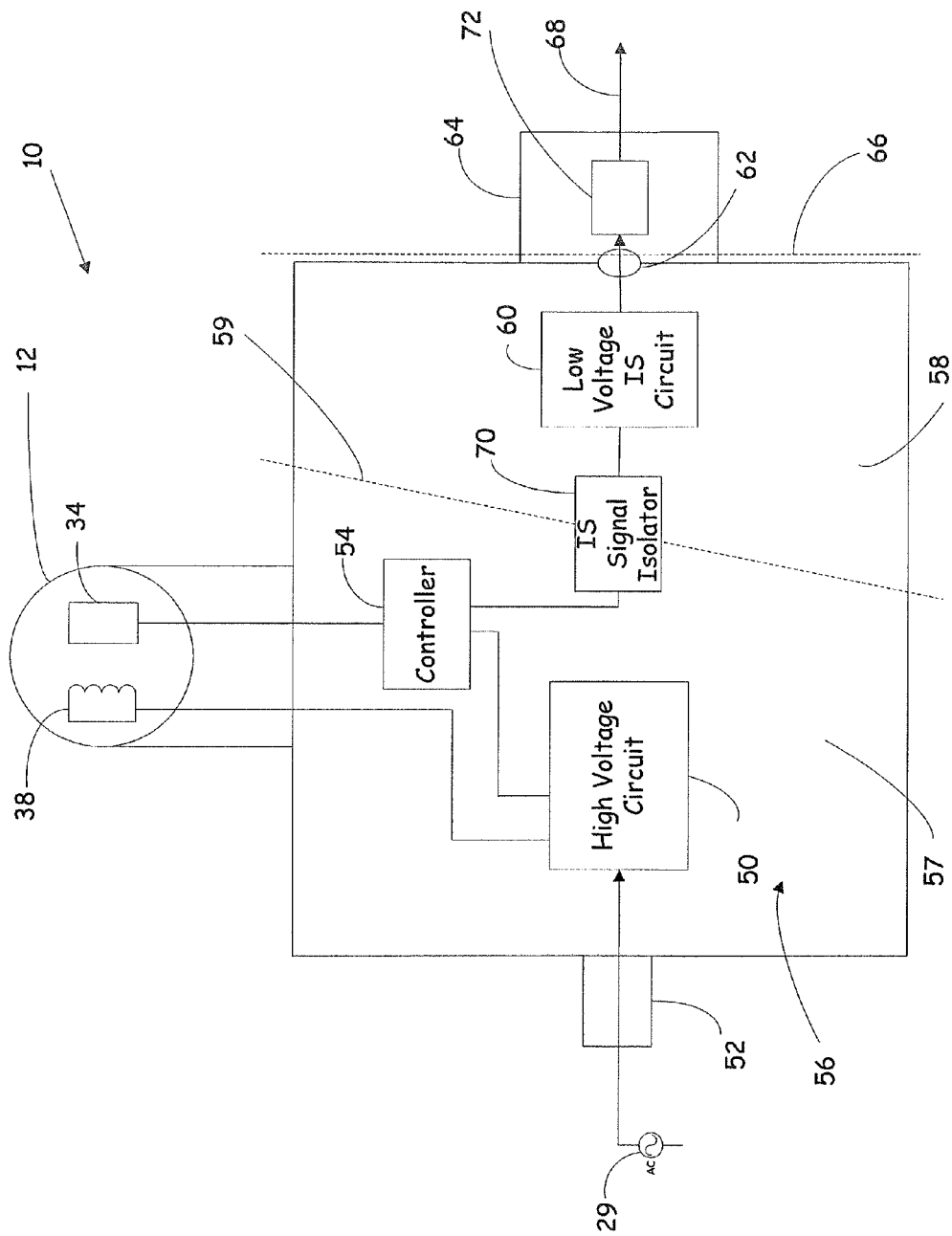
FIG. 3 is a diagrammatic view of an in situ heated oxygen probe having an intrinsically safe output in accordance with an embodiment of the present invention.

FIG. 3 is a diagrammatic view of an in situ heated oxygen probe having an intrinsically safe output in accordance with an embodiment of the present invention. Probe 12 includes sensor cell 34 positioned for exposure to flue gas or exhaust. Since sensor cell 34 operates at an elevated temperature and provides an indication of oxygen concentration to controller 54, heater assembly 38 is coupled to high voltage circuit 50 and is disposed to provide heat to sensor cell 34, such that sensor cell 34 can be maintained at the requisite elevated temperature. In one embodiment, sensor cell 34 includes a zirconium oxide sensor and the requisite temperature is about 700° Celsius. Controller 54 is also coupled to high voltage circuit 50 such that controller 54 can control the energization of heater assembly 38 to maintain sensor cell 34 at the requisite temperature. Controller 54 can be any suitable device or component, but, in one embodiment, is a microprocessor.

Analyzer 10 is coupled to AC source 29 through explosion-rated conduit 52. Since conduit 52 is explosion-rated, it prevents gases from entering housing 36. Moreover, if gases do enter housing 36 and ignite via contact with high voltage circuit 50 or any other component within housing 36, the flame cannot escape the housing. In the embodiment shown in FIG. 3, all of housing 36 is explosion-rated. However, embodiments of the present invention can be practiced where the intrinsically-safe portion (chamber 64, described below) of housing 36 is not explosion-proof. An explosion-proof wiring feed-through 62 couples low voltage intrinsically-safe circuit 60 to intrinsically-safe circuitry 72 in chamber 64 through intrinsic safety boundary or barrier 66. Circuitry 72 can be any intrinsically-safe circuitry or components. For example, circuitry 72 may be a simple board with customer terminals and a fuse and some basic protective circuitry. However, circuitry 72 may also include all of the circuitry necessary to comprise an intrinsically-safe transmitter with its own process communication capabilities. Such process communication capabilities include communication in accordance with the Highway Addressable Remote Transducer (HART®) protocol, the FOUNDATION™ Fieldbus protocol or other process communication protocols.

Since chamber 56 is explosion-proof, a flame or explosion within chamber 56 cannot escape through feed-through 62 and thus will not ignite or otherwise damage the safe area. Signal line 68 allows device 10 to communicate with one or more other devices in an energy-limited manner to comply with intrinsic safety specifications. Intrinsically-safe circuit 60 can include any suitable circuitry that is operable in compliance with an intrinsic safety specification. In one embodiment, circuit 60 may include communication circuitry for generating energy-limited signal suitable for conveyance through hazardous environments in accordance with a process communication protocol.

In accordance with an embodiment of the present invention, housing 36 has a pair of chambers 56, 64 therein. While the embodiment shown in FIG. 3 depicts chambers 56 and 64 adjacent one another, embodiments of the present invention can be practiced where chambers 56 and 64 are spaced apart. In embodiments where chambers 56 and 64 are spaced apart, explosion-proof wiring feed-through is an explosion-rated conduit. Chamber 56 has a non-intrinsically-safe region 57 and an intrinsically-safe region 58. Chamber 56 houses high voltage circuit 50 in region 57 as well as any other non-intrinsically-safe circuitry used in analyzer 10. In contrast, region 58 and chamber 64 house only circuitry that complies with an intrinsic safety specification, such as that set forth above. Regions 57 and 58 are separated by imaginary line 59. The intrinsically-safe circuitry on the right of line 59 is fed to chamber 64 using explosion-proof wiring feed-through 62. The signal passing through feed-through 62 may be conveyed along wires or in any other suitable manner, such as light, fiber-optic, magnetic, radio-frequency, et cetera. While dashed line 59 represents separation between non-intrinsically-safe circuitry and intrinsically-safe circuitry on the same printed circuit board, such separation can also be accomplished using separate printed circuit boards. Moreover any acceptable techniques for separating the non-intrinsically-safe circuitry from the intrinsically-safe circuitry can be used. In this embodiment, the only way in which signals are passed between circuitry 50 in region 57 and circuitry 60 in region 58 is through signal isolator 70. Isolator 70 ensures that signals passing through isolator 70 are energy limited. In one example, isolator 70 provides 250 volt intrinsically-safe signal isolation that meets the requirements of intrinsic safety to separate intrinsically safe circuits from non-intrinsically-safe circuits.

Embodiments of the present invention thus provide an in situ oxygen analyzer that has the advantages of using an electrical heater to heat the oxygen sensor to the temperature required for useful operation (typically over 600° Celsius) while still providing the convenience of intrinsically-safe wiring. This allows the user to employ simpler intrinsically-safe wiring techniques from the device to the distributed control system.

Although the present invention has been described with reference to preferred embodiments, workers skilled in the art will recognize that changes may be made in form and detail without departing from the spirit and scope of the invention. For example, while the present invention has been described with respect to an in situ oxygen analyzer having a heated oxygen sensor, embodiments of the present invention can be applied to any instrument or device that requires such power that at least a portion of the instrument or device cannot comply with intrinsic safety requirements, but wherein an intrinsically-safe output is desired.

What is claimed is:

1. An in situ oxygen analyzer comprising:
a probe extendable into a source of process gas, the probe having an oxygen sensor and heater disposed therein, wherein the heater is configured to heat the oxygen sensor to a temperature sufficient to operate the oxygen sensor;
a housing coupled to the probe, the housing having first and second chambers therein, the first chamber being explosion-rated and including non-intrinsically safe circuitry coupled to the heater to energize the heater, the second chamber containing only intrinsically-safe circuitry that complies with an intrinsically-safe specification; and
wherein the first and second chambers are coupled together by an explosion-rated feed-through and wherein the non-intrinsically-safe circuitry is isolated from the intrinsically-safe circuitry through an energy-limiting isolator.

2. The in situ oxygen analyzer of claim 1, and further comprising an explosion-rated conduit configured to couple the non-intrinsically-safe circuitry to a source of power.

3. The in situ oxygen analyzer of claim 1, wherein the entire housing is explosion-rated.

4. The in situ oxygen analyzer of claim 1, wherein the non-intrinsically-safe circuitry includes a controller operably coupled to the oxygen sensor, wherein the controller is configured to control the heater to maintain the oxygen sensor at the temperature sufficient to operate the oxygen sensor.

5. The in situ oxygen analyzer of claim 4, wherein the oxygen sensor is a zirconium oxygen sensor and wherein the temperature is over 600° Celsius.

6. The in situ oxygen analyzer of claim 1, wherein the intrinsically-safe circuitry includes communication circuitry.

7. The in situ oxygen analyzer of claim 1, wherein the energy-limiting isolator is at least a 250 volt intrinsically-safe signal isolator.

8. The in situ oxygen analyzer of claim 1, wherein the second chamber is configured to be disposed on an opposite side of an intrinsic safety boundary from the first chamber.

9. The in situ oxygen analyzer of claim 1, wherein the first chamber has a first region containing non-intrinsically-safe circuitry and a second region containing only intrinsically-safe circuitry.

10. The in situ oxygen analyzer of claim 9, wherein the energy-limiting isolator is disposed between the non-intrinsically safe circuitry of the first region and the intrinsically-safe circuitry in the second region.

11. The in situ oxygen analyzer of claim 9, wherein the intrinsically safe circuitry of the second chamber is connected to the intrinsically safe circuitry of the second region of the first chamber through the explosion-rated feed-through.

12. The in situ oxygen analyzer of claim 9, wherein the first and second regions are disposed on a single circuit board.

13. The in situ oxygen analyzer of claim 9, wherein the first and second regions are disposed on different circuit boards.

14. The in situ oxygen analyzer of claim 9, wherein the first and second chambers are spaced apart.

* * * * *